United States Patent [19]

Salbeck et al.

[11] 4,152,428

[45] May 1, 1979

[54] PESTICIDAL AGENTS

[75] Inventors: Gerhard Salbeck, Hofheim;
Hubert Schonowsky, Urberach;
Gerhard Horlein, Frankfurt am Main;
Ludwig Emmel, Bergen-Einkheim;
Anna Waltersdorfer, Frankfurt am Main, all of Fed. Rep. of Germany

[73] Assignee: Hoechst Aktiengesellschaft, Frankfurt am Main, Fed. Rep. of Germany

[21] Appl. No.: 789,722

[22] Filed: Apr. 21, 1977

[30] Foreign Application Priority Data

Apr. 23, 1976 [DE] Fed. Rep. of Germany ....... 2617736

[51] Int. Cl.² .......................... A01N 9/36; C07F 9/40
[52] U.S. Cl. .................................... 424/211; 260/943
[58] Field of Search ........................ 260/943; 424/211

[56] References Cited

U.S. PATENT DOCUMENTS

| 3,032,466 | 5/1962 | Schuler | 260/943 X |
| 3,032,579 | 5/1962 | Losco et al. | 260/943 X |
| 3,053,729 | 9/1962 | Sun | 260/943 UX |
| 3,057,774 | 10/1962 | Baker et al. | 260/943 X |

*Primary Examiner*—Anton H. Sutto
*Attorney, Agent, or Firm*—Curtis, Morris & Safford

[57] ABSTRACT

Compounds of the formula

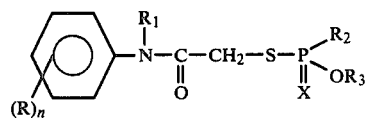

in which R represents halogen, $C_1$–$C_6$-alkyl, $C_1$–$C_3$-haloalkyl, $NO_2$, $C_1$–$C_4$-thioalkyl or $OCH_3$, $R_1$, $R_2$ and $R_3$ represent $C_1$–$C_6$-alkyl, X is oxygen or sulfur and n is a whole number in the range of from 1 to 3 exhibit good insecticidal, acaricidal and nematodicidal properties.

11 Claims, No Drawings

PESTICIDAL AGENTS

The subject of the present application is compounds of the general formula

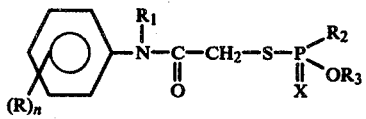

in which
R = identical or different substituents selected from the group halogen, $(C_1-C_6)$-alkyl, $(C_1-C_3)$-halogenoalkyl, $NO_2$, $(C_1-C_4)$-thioalkyl and $OCH_3$,
$R_1$, $R_2$ and $R_3$ = $(C_1-C_6)$-alkyl (identical or different),
X = oxygen or sulfur and
n = an integer of from 1 to 3.
with the proviso that $(R)_n$ cannot be 4-chlorine when $R_1$ is methyl.

Compounds of the formula I, in which R = $CH_3$ and $R_2$ = alkyl are covered in general form by U.S. Pat. specification No. 3,057,774, but are not described in detail. A few analogously constructed phosphoric acid esters are furthermore known from German Auslegesschrift No. 1,122,935, but have a lower insecticidal and miticidal activity than the compounds according to the invention (cf. Example VI).

Preferred radicals of the general formula I are R = F, Cl, Br, $(C_1-C_4)$-alkyl, $CF_3$, $NO_2$ and $S-CH_3$ $R_1$, $R_2$, and $R_3$ = $(C_1-C_4)$-alkyl. Especially preferred for R are F, Cl, Br, $(C_1-C_3)$alkyl, $NO_2$ and $S-CH_3$.

The subject of the invention is furthermore insecticides that contain as active substance compounds of the formula I in addition to customary formulation auxiliaries and inert substances.

The compounds of the formula (I) are obtained in a manner known per se in that (a) compounds of the formula

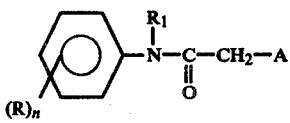

are reacted, if necessary in the presence of an acid-binding agent, with phosphorus compounds of the formula

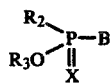

wherein in each case one of the radicals A and B represents a halogen, in particular chlorine or bromine, and the other represents the SY-group, in which Y is hydrogen or a metal cation, or (b) first of all compounds of the formula IV

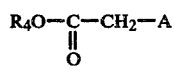

are reacted with compounds of the formula III and the intermediate products of the formula V obtained

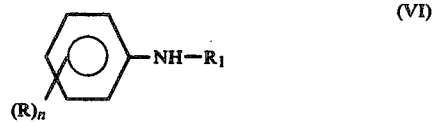

are converted, by reacting with anilines of the formula VI into compounds of the formula I in which $R_4$ preferably represents a lower alkyl or phenyl.

(a) The phosphorus compounds of the formula III (B = SY) react with the chloroacetanilides of the formula II (A = hal) without difficulty, advantageously at temperatures of between 0° and +120° C., preferably +10° to +80° C.

It is advisable to carry out the process according to the invention in the presence of a solvent or diluent inert with respect to the reactants. There come into consideration chiefly lower aliphatic ketones, such as acetone or methylethyl ketone, alkanols such as methanol, ethanol or isopropanol, esters such as ethyl acetate, nitriles, N-alkylated acid amides such as dimethyl formamide, ethers such as dioxane, glycoldimethyl ether or tetrahydrofuran, chlorinated hydrocarbons such as chloroform or carbon tetrachloride and water as well as mixtures of such solvents.

The reaction takes place with the exchange of the halogen atom of the chloroacetanilides. Therefore, the reaction is conducted either with the addition of acid-binding agents or with the salts, in particular with alkali metal salts and ammonium salts, of the phosphorus compounds. Alkali metal hydroxides and carbonates are preferred as acid-binding agent; it is also possible, however, to use tertiary nitrogen bases such as pyridine or triethyl amine.

The haloacetic acid anilides of the formula II and their manufacture are described in the literature.

The SY-compounds according to formula II are known and can be obtained easily according to customary methods.

Conversely, it is also possible to react thioglycolic acid anilides (formula II, A = SY) with halophosphorus compounds (formula III, B = hal), wherein when $R_4$ = SH the reaction is carried out likewise in the presence of an acid-binding agent. Generally approximately stoichiometric amounts of the reactants are used, but an excess of the compound of formula III of 5-10% can be advantageous.

The reaction is preferably carried out in the presence of a solvent that is inert under the reaction conditions. As a solvent of this type it is possible to use, for example, any of those mentioned above. The reaction temperatures may be varied within a wide range, but preferably temperatures of between +50° and +120° C. are used. It is likewise possible to use as acid-binding agent any of those mentioned above.

The thioglycolic acid anilides according to formula II may be produced according to methods known in the literature. The halophosphorus compounds of the formula III are known and can be obtained according to customary methods.

(b) The process (b) proceeds in the first stage (reaction of III with IV) in accordance with process (a). The intermediate product of the formula V can be subjected directly to amination without isolation, i.e. in a one vessel process, wherein it is possible to operate at temperatures of 0°–150° C. The reaction temperature depends in this case on the reactivity of the radical $OR_4$; activated esters, such as, for example, phenyl esters, react at lower temperatures.

The compounds of the formula I have insecticidal, miticidal and nematocidal properties.

The claimed compounds of the formula I are effective as insecticidal and miticidal agents both by means of contact and by eating, and are thus suitable for destroying numerous pests and their stages of development on a wide variety of crops whilst at the same time being well tolerated by plants. It is possible to combat well different types of spider mites, such as the fruit tree spider mite (Metatetraanychus ulmi), the citrus spider mite (Panonychus citri) and the bean spider mite (Tetranychus urticae) as well as, also, strains that are resistant to phosphoric acid esters.

To some extent the compounds of the formula I exhibit a good penetrating action in plants. The result of this is, for example, that pests on the underside of the leaves are killed, even if only the upper side has been treated.

It is possible to destroy a large number of insects that are damaging to crops with their sucking and biting actions by using the compounds according to the invention. The following pests may be mentioned: beetles such as the Mexican bean beetle (*Epilachna varivestis*), the Colorado beetle (*Leptinotarsa decemlineata*), villous flower beetle (*Epicometis hirta*), flea beetles (Phyllotreta spp.), strawberry stem borers (*Coenorrhinus germanicus*) and boll weevil (Anthonomus grandis), butterflies and their larvae such as the Egyptian and European boll weevil (*Earias insulana* and *Heliothis armisgera*), tortricidae, especially apple tortrix (*Carpocapsa pomonella*), oak tortrix (*Tortrix viridana*), fruit peel tortrix (*Adoxophyes reticulana*), corn borer (*Ostrinia nubilalis*) and Cheimatobia (*Operophthera brumata*), aphids, such as the black bean aphid (*Doralis fabae*), green peach aphid (*Myzodes persicae*) and cotton aphids (*Aphis gossypi*) and plant-sucking bugs, for example, cotton stainers (Oncopeltus and Dysderus spp., especially fasciatus). Furthermore, shield ticks on domestic animals are combatted for example, *Hyalomm marginatum, Rhipicephalus evertsi, Amblyomma Hebraeum* and *Boophilus microplus*.

Furthermore, the compounds have an excellent action against plant-damaging nematodes, for example those of the meloidogyne, heterodera, ditylenchus and aphelenchoid types.

Also advantageous are the comparatively favourable toxicities towards warm-blooded animals, especially of the halogen-substituted compounds, in comparison with analogous phosphoric acid esters unsubstituted in the aromatic nucleus.

The agents according to the invention generally contain 2–80% of the active substances of the formula I. They can be applied in the form of wettable powders, emulsifiable concentrates, sprayable solutions, dusting agents or granulates in the customary preparations.

Wettable powders are preparations that are uniformly dispersible in water that in addition to the active substance contain, apart from a diluent or inert substance, wetting agents, for example, polyoxethylated alkyl phenols, polyoxethylated oleyl or stearyl amines, alkyl or alkylphenyl sulfonates and dispersing agents, for example the sodium salts of ligninsulfonic acid and of 2,2'-dinaphthylmethane-6,6'-disulfonic acid, or also of oleylmethyl taurine.

Emulsifiable concentrates are obtained by dissolving the active substance in an organic solvent, for example butanol, cyclohexanone, dimethyl formamide, xylene or also aromatic substances of higher boiling points.

Dusting agents are obtained by grinding the active substance with finely divided solid substances, for example talcum, natural clays, such as kaolin, bentonite, pyrophyllite or diatomaceous earths.

Sprayable solutions, as handled a great deal in spray packs, contain the active substance dissolved in an organic solvent, and in addition a mixture of, for example, fluorochlorohydrocarbons as propellant.

Granulates can be produced either by spraying the active substance onto adsorptive, granulated inert material, or by applying active substance concentrates by means of adhesives, for example polyvinyl alcohol, the sodium salt of polyacrylic acid or even mineral oils, to the surface of carrier materials, such as sand, kaolinites or to the surface of granulated inert material. Also, suitable active substances can be produced in the manner customary for the production of fertilizer granules, - if desired in admixture with fertilizers.

The concentration of active substance in wettable powders varies, for example, between approximately 10% and 80%, the rest consisting of the above-mentioned formulation additives. The concentration of active substance in emulsifiable concentrates is approximately 10% to 70%. Dust formulations usually contain 5–20% of active substance, and sprayable solutions approximately 2–20% of active substance. The content of active substance in granulates depends to some extent on whether the active compound is liquid or solid and on which granulate auxiliaries, fillers, etc are used.

For use, the commercially customary concentrates are, if necessary, diluted in the usual manner, for example in the case of wettable powders and emulsifiable concentrates by means of water. Dust-type and granulated preparations, as well as sprayable solutions, are not diluted further with inert substances before use.

To combat nematodes, the active substances may be applied to the soil to be treated in the form of dusts, granulates or aqueous suspensions, and subsequently worked into the soil by hoeing or using a rotary hoe. If volatile agents are used, the soil must be handled accordingly.

The active substance according to the invention can be combined with other insecticides, fungicides, nematocides and herbicides.

The following examples illustrate the invention.

FORMULATION EXAMPLES

EXAMPLE A

A wettable powder, easily dispersible in water, is obtained by mixing 25 parts by weight of methanedithiophosphonic acid-S-[N-(4-chlorophenyl)-N-isopropylcarbamoylmethyl]-O-ethyl ester as active substance, 64 parts by weight of kaolin-containing quartz as inert substance, 10 parts by weight of a potassium salt of ligninsulfonic acid and 1 part by weight of a sodium salt of oleylmethyltaurine as wetting and dispersing agent and grinding the mixture in a pin mill.

EXAMPLE B

A dusting agent suitable for use is obtained by mixing
10 parts by weight of methanedithiophosphonic acid-S-[N-(4-chlorophenyl)-N-isopropylcarbamoylmethyl]-O-ethyl ester as active substance and
90 parts by weight of talcum as inert substance and pulverising the mixture in a hammer mill.

EXAMPLE C

An emulsifiable concentrate consists of
15 parts by weight of methanedithiophosphonic acid-S-[N-(4-chlorophenyl)-N-isopropylcarbamoylmethyl]-O-ethyl ester as active substance,
75 parts by weight of cyclohexanone as solvent and
10 parts by weight of oxethylated nonylphenol (10 EO) as emulsifier.

EXAMPLE D

A granulate consists, for example, of approximately 2–15 parts by weight of methanedithiophosphonic acid-S-[N-(4-chlorophenyl)-N-isopropylcarbamoyl]-O-ethyl ester as active substance
and an inert granulate carrier material such as, for example, attapulgite, pumice granulate and/or quartz sand.

EXAMPLES OF PRODUCTION

General directions:

(A) 0.1 mole of a chloroacetanilide of the formula II (A = Cl) is added at room temperature, while stirring, to a solution or suspension of 0.10–0.11 mole of an ammonium salt of a phosphorus compound of the formula III (B = SNH$_4$) in 200 ml of glycoldimethyl ether. Stirring is carried out for approximately 3–5 hours at 50° C., the precipitated salt suction filtered, the filtrate diluted with approximately 400 ml of benzene, the organic phase washed thoroughly with water and dried over sodium sulfate. After distilling off the solvent the products of the process are left in the form of oils, which partially crystallise on triturating.

The same result is obtained if, instead of glycoldimethyl ether, another of the solvents mentioned under (a) on page 3 is used or if the reaction is carried out at elevated temperature (+80° C.).

(B) 0.1 mole of a thioglycolic acid anilide of the formula II (A = SH) is added at 50°–120° C., while stirring, to a solution or suspension of 0.10–0.11 mole of a (thio)phosphonic acid chloride of the formula III (B = Cl) in 200 ml of glycoldimethyl ether, in the presence of an acid-binding agent. Stirring is carried out for a few hours at 80°–120° C., then the procedure is as under A).

The same result is obtained if, instead of glycoldimethyl ether, another of the solvents mentioned under a) on page 4 is used.

C. 1st Stage 0.2 mole of thioglycolic acid methyl ester and 0.2 mole of methyl-O-ethyl-thiophosphonic acid chloride are dissolved in 250 ml of toluene and 0.21 mole of triethylamine are added dropwise, while stirring, at 0°–5° C. Once the dropwise addition is complete, stirring is carried out for 2 hours at room temperature. The precipitated triethylamine hydrochloride is suction filtered, the filtrate is washed with water, dried and concentrated in vacuo. The desired compound of the formula V (R$_4$ = CH$_3$, R$_2$ = CH$_3$, R$_3$ = C$_2$H$_5$) is yielded in the form of a yellow oil.

The compound V can also be produced in the following manner:

0.2 mole of chloroacetic acid methyl ester are added dropwise at 10°–15° C. to a solution of 0.21 mole of ammonium-methyl-O-ethyl-dithiophosphonate in 250 ml of glycoldimethylether. The mixture is stirred for 3 hours at room temperature, then 0.5 l of toluene is added and the whole is washed three times with water. The organic phase is dried over Na$_2$SO$_4$ and concentrated in vacuo.

2nd Stage

A solution of 0.2 mole of 4-chloro-N-isopropylaniline is added dropwise to a solution of 0.2 mole of the compound V in 300 ml of glycoldimethyl ether, and the whole is boiled under reflux for 5 hours. Subsequently the whole is concentrated in vacuo and 0.3 l of toluene is added to the residue, this mixture is then washed with 10% aqueous hydrochloric acid, washed with water until neutral, dried over Na$_2$SO$_4$ and concentrated in vacuo.

The desired compound 15 in the Table is obtained in this manner.

The compounds of the formula I listed in the following Table were obtained according to the above-described process, their composition was confirmed by elemental analysis, and they are characterised by refractive index and/or melting point:

Table

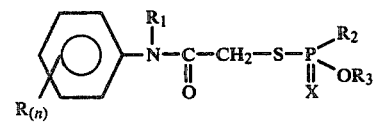

| Example | R$_{(n)}$ | R$_1$ | R$_2$ | R$_3$ | X | n$_D$ or Mp. |
|---|---|---|---|---|---|---|
| 1 | 4-F | —CH(CH$_3$)$_2$ | —CH$_3$ | —CH$_3$ | S | n$_D^{23}$ : 1.5565 |
| 2 | 4-F | —CH(CH$_3$)$_2$ | —CH$_3$ | —C$_2$H$_5$ | S | n$_D^{23}$ : 1.5498 |
| 3 | 4-F | —CH(CH$_3$)$_2$ | —C$_2$H$_5$ | —C$_2$H$_5$ | S | n$_D^{24}$ : 1.5454 |
| 4 | 4-F | —CH(CH$_3$)$_2$ | —CH$_3$ | —C$_4$H$_9$(i) | S | n$_D^{24}$ : 1.5393 |
| 5 | 4-F | —CH(CH$_3$)$_2$ | —C$_4$H$_9$(i) | —C$_4$H$_9$(i) | S | n$_D^{23}$ : 1.5282 |
| 6 | 4-F | —CH(CH$_3$)$_2$ | —CH$_3$ | —C$_4$H$_9$(i) | O | n$_D^{23}$ : 1.5132 |
| 7 | 2-Cl | —CH$_3$ | —CH$_3$ | —C$_2$H$_5$ | S | n$_D^{24}$ : 1.5725 |
| 8 | 3-Cl | —CH$_3$ | —CH$_3$ | —C$_2$H$_5$ | S | Mp. 53–55° C. |
| 9 | 4-Cl | —CH$_3$ | —CH$_3$ | —C$_2$H$_5$ | S | n$_D^{23}$ : 1.5830 |
| 10 | 4-Cl | —C$_2$H$_5$ | —CH$_3$ | —C$_2$H$_5$ | S | n$_D^{25}$ : 1.5767 |
| 11 | 4-Cl | —C$_2$H$_5$ | —CH$_3$ | —C$_4$H$_9$(i) | O | n$_D^{28}$ : 1.5313 |
| 12 | 4-Cl | —C$_2$H$_5$ | —C$_4$H$_9$(i) | —C$_2$H$_5$ | S | n$_D^{25}$ : 1.5610 |
| 13 | 4-Cl | —CH(CH$_3$)$_2$ | —CH$_3$ | —CH$_3$ | S | n$_D^{23}$ : 1.5715 |
| 14 | 4-Cl | —CH(CH$_3$)$_2$ | —CH$_3$ | —C$_4$H$_9$(i) | O | n$_D^{25}$ : 1.5255 |

Table-continued $$\underset{R_{(n)}}{\bigodot}-N(R_1)-\underset{O}{\overset{\|}{C}}-CH_2-S-\underset{X}{\overset{\|}{P}}(R_2)(OR_3)$$

| Example | $R_{(n)}$ | $R_1$ | $R_2$ | $R_3$ | X | $n_D$ or Mp. |
|---|---|---|---|---|---|---|
| 15 | 4-Cl | —CH(CH$_3$)$_2$ | —CH$_3$ | —C$_2$H$_5$ | S | $n_D^{25}$: 1.5624 |
| 16 | 4-Cl | —CH(CH$_3$)$_2$ | —C$_4$H$_9$(i) | —C$_4$H$_9$(i) | S | $n_D^{26}$: 1.5455 |
| 17 | 4-Cl | —C$_2$H$_5$ | —CH$_3$ | —C$_4$H$_9$(i) | S | $n_D^{24}$: 1.5630 |
| 18 | 4-Cl | —C$_4$H$_9$(sek) | —CH$_3$ | —$n_D^2$H$_5$ | S | $n_D^{24}$: 1.5610 |
| 19 | 4-Cl | —C$_4$H$_9$(sek) | —CH$_3$ | —C$_4$H$_9$(i) | S | $n_D^{24}$ 1.5530 |
| 20 | 4-Cl | —C$_4$H$_9$(sek) | —CH$_3$ | —C$_4$H$_9$(i) | O | $n_D^{24}$ 1.5271 |
| 21 | 4-Cl | —C$_4$H$_9$(sek) | —C$_4$H$_9$(n) | —C$_2$H$_5$ | S | $n_D^{24}$: 1.5533 |
| 22 | 4-Br | —CH(CH$_3$)$_2$ | —CH$_3$ | —C$_4$H$_9$(i) | S | $n_D^{28}$ 1.5636 |
| 23 | 4-Br | —CH(CH$_3$)$_2$ | —CH$_3$ | —C$_2$H$_5$ | S | $n_D^{23}$: 1.5783 |
| 24 | 4-Br | —CH(CH$_3$)$_2$ | —CH$_3$ | —C$_4$H$_9$(i) | O | $n_D^{23}$: 1.5400 |
| 25 | 4-Br | —CH(CH$_3$)$_2$ | —C$_4$H$_9$(n) | —C$_2$H$_5$ | S | $n_D^{24}$: 1.5676 |
| 26 | 2,3-Cl | —CH$_3$ | —CH$_3$ | —C$_2$H$_5$ | S | $n_D^{21}$: 1.6012 |
| 27 | 2,4-Cl | —CH$_3$ | —CH$_3$ | —C$_2$H$_5$ | S | $n_D^{24}$: 1.5902 |
| 28 | 2,5-Cl | —CH$_3$ | —CH$_3$ | —C$_2$H$_5$ | S | $n_D^{27}$: 1.6003 |
| 29 | 3,4-Cl | —CH$_3$ | —CH$_3$ | —C$_2$H$_5$ | S | Mp. 94° C. |
| 30 | 3,5-Cl | —CH$_3$ | —CH$_3$ | —C$_2$H$_5$ | S | Mp. 84–86° C. |
| 31 | 3-CF$_3$ | —CH(CH$_3$)$_2$ | —CH$_3$ | —C$_2$H$_5$ | S | $n_D^{22}$ 1.5228 |
| 32 | 3-CF$_3$ | —CH(CH$_3$)$_2$ | —CH$_3$ | —C$_4$H$_9$(i) | O | $n_D^{25}$: 1.4890 |
| 33 | 3-CF$_3$ | —CH(CH$_3$)$_2$ | —CH$_3$ | —C$_4$H$_9$(i) | S | $n_D^{22}$: 1.5145 |
| 34 | 3-CF$_3$ | —C$_4$H$_9$(sek) | —CH$_3$ | —C$_2$H$_5$ | S | $n_D^{24}$: 1.5200 |
| 35 | 3-CF$_3$ | —C$_4$H$_9$(sek) | —CH$_3$ | —C$_4$H$_9$(i) | O | $n_D^{25}$: 1.4910 |
| 36 | 3-CF$_3$ | —C$_4$H$_9$(sek) | —CH$_3$ | —C$_4$H$_9$(i) | S | $n_D^{25}$: 1.5135 |
| 37 | 3-CF$_3$ | —C$_4$H$_9$(sek) | —C$_4$H$_9$(n) | —C$_2$H$_5$ | S | $n_D^{24}$: 1.5151 |
| 38 | 4-NO$_2$ | —CH$_3$ | —CH$_3$ | —C$_4$H$_9$(i) | O | $n_D^{24}$: 1.5590 |
| 39 | 2-NO$_2$ | —CH$_3$ | —CH$_3$ | —C$_2$H$_5$ | S | $n_D^{23}$: 1.5882 |
| 40 | 3-NO$_2$ | —CH$_3$ | —CH$_3$ | —C$_2$H$_5$ | S | $n_D^{25}$: 1.5914 |
| 41 | 4-NO$_2$ | —C$_2$H$_5$ | —CH$_3$ | —C$_2$H$_5$ | S | Mp. 65–68° C. |
| 42 | 4-NO$_2$ | —CH(CH$_3$)$_2$ | —CH$_3$ | —C$_2$H$_5$ | S | $n_D^{25}$: 1.5732 |
| 43 | 4-NO$_2$ | —C$_4$H$_9$(n) | —CH$_3$ | —C$_2$H$_5$ | S | $n_D^{25}$: 1.5853 |
| 44 | 4-NO$_2$ | —CH$_3$ | —C$_2$H$_5$ | —C$_2$H$_5$ | S | Mp. 61–66 |
| 45 | 4-CH(CH$_3$)$_2$ | —CH(CH$_3$)$_2$ | —C$_2$H$_5$ | —C$_2$H$_5$ | S | $n_D^{23}$: 1.5494 |
| 46 | 4-OCH$_3$ | —CH(CH$_3$)$_2$ | —CH$_3$ | —C$_2$H$_5$ | S | $n_D^{27}$: 1.5592 |
| 47 | 4-OCH$_3$ | —CH(CH$_3$)$_2$ | —CH$_3$ | —C$_4$H$_9$(i) | S | $n_D^{27}$: 1.5482 |
| 48 | 4-OCH$_3$ | —CH(CH$_3$)$_2$ | —CH$_3$ | —C$_4$H$_9$(i) | O | $n_D^{24}$: 1.5262 |
| 49 | 4-CH$_3$ | —CH(CH$_3$)$_2$ | —CH$_3$ | —C$_2$H$_5$ | S | $n_D^{27}$: 1.5453 |
| 50 | 4-CH$_3$ | —CH(CH$_3$)$_2$ | —CH$_3$ | —C$_4$H$_9$(i) | S | $n_D^{27}$: 1.5560 |
| 51 | 2-CH(CH$_3$)$_2$ | —CH(CH$_3$)$_2$ | —CH$_3$ | —CH$_3$ | S | $n_D^{25}$: 1.5575 |
| 52 | 2-CH(CH$_3$)$_2$ | —CH(CH$_3$)$_2$ | —CH$_3$ | —C$_2$H$_5$ | S | Mp. 64–66° C. |
| 53 | 2-CH(CH$_3$)$_2$ | —CH(CH$_3$)$_2$ | —CH$_3$ | —C$_4$H$_9$(i) | O | $n_D^{23}$: 1.5223 |
| 54 | 2-CH(CH$_3$)$_2$ | —CH(CH$_3$)$_2$ | —CH$_3$ | —C$_4$H$_9$(i) | S | $n_D^{23}$: 1.5420 |
| 55 | 4-CH(CH$_3$)$_2$ | —CH(CH$_3$)$_2$ | —CH$_3$ | —C$_2$H$_5$ | S | $n_D^{25}$: 1.5542 |
| 56 | 4-C(CH$_3$)$_3$ | —CH(CH$_3$)$_2$ | —CH$_3$ | —C$_2$H$_5$ | S | Mp. 54–59° C. |
| 57 | 4-C(CH$_3$)$_3$ | —CH(CH$_3$)$_2$ | —CH$_3$ | —C$_4$H$_9$(i) | S | Mp. 64–73° C. |

EXAMPLES OF APPLICATION

EXAMPLE I

Bean crops (*Phaseolus vulgaris*) strongly affected by the spider mite *Tetranychus urticae* (normal sensitivity) were sprayed, until drip-off, with the aqueous dilution of an emulsion concentrate that contained 0.0015% by weight of the active substance of Example (1). Subsequently the sprayed plants were placed in a greenhouse at approximately 20° C. The microscopic check 8 days after spraying showed that all moving and non-moving stages were dead.

When tested in the same manner, the compounds given in Table 1 proved equally effective.

Table 1

| Preparation according to Example | % by weight AS in the spray liquor | miticidal action in % mortality |
|---|---|---|
| 2 | 0.00075 | 100 |
| 3 | 0.003 | 100 |
|   | 0.0015 | 95 |
| 4 | 0.003 | 100 |
|   | 0.0015 | 94 |
| 7 | 0.0015 | 100 |
| 8 | 0.00075 | 93 |
|   | 0.003 | 100 |
|   | 0.0015 | 90 |
| 9 | 0.0015 | 100 |
| 10 | 0.00075 | 95 |
|   | 0.003 | 100 |
|   | 0.0015 | 97 |
| 13 | 0.0015 | 97 |
| 15 | 0.0015 | 100 |
| 17 | 0.0015 | 100 |
| 18 | 0.00075 | 80 |
|   | 0.003 | 100 |
|   | 0.0015 | 80 |
| 23 | 0.0015 | 100 |
| 26 | 0.00075 | 97 |
|   | 0.0015 | 100 |
| 27 | 0.00075 | 95 |
|   | 0.000375 | 100 |
|   | 0.00019 | 95 |
| 31 | 0.003 | 100 |
|   | 0.0015 | 98 |
| 33 | 0.006 | 100 |
|   | 0.003 | 98 |
| 34 | 0.006 | 100 |

Table 1-continued

| Preparation according to Example | % by weight AS in the spray liquor | miticidal action in % mortality |
|---|---|---|
|  | 0.003 | 96 |
| 39 | 0.003 | 100 |
|  | 0.0015 | 98 |
| 40 | 0.003 | 100 |
|  | 0.0015 | 85 |
| 46 | 0.003 | 95 |
|  | 0.0015 | 80 |
| 49 | 0.003 | 95 |
|  | 0.0015 | 80 |
| 51 | 0.0015 | 100 |
|  | 0.00075 | 80 |
| 52 | 0.003 | 100 |
|  | 0.0015 | 90 |
| 54 | 0.006 | 100 |
|  | 0.003 | 60 |
| 60 | 0.0015 | 100 |
|  | 0.00075 | 80 |
| 63 | 0.0015 | 100 |
|  | 0.00075 | 80 |
| 67 | 0.0015 | 100 |
|  | 0.00075 | 70 |
| 68 | 0.0015 | 100 |
|  | 0.00075 | 60 |

EXAMPLE II

Plants (*Phaseolus vulgaris*) infected with resistant spider mites were sprayed with aqueous suspensions of spray powder concentrates of the compounds given in the following Table II until drip-off. After placing the plants in the greenhouse at 20° C., a check was made after 8 days.

Table II

| Preparation according to Example | $LC_{99/100}{}^{2)}$ Tu (B)[1)] |
|---|---|
| 2 | 0.0125 |
| 3 | 0.0125 |
| 9 | 0.0125 |
| 10 | 0.006 |
| 13 | 0.0125 |
| 15 | 0.006 |
| 23 | 0.0125 |
| 31 | 0.0125 |
| 34 | 0.0125 |
| 51 | 0.0015 |
| 52 | 0.003 |
| 58 | 0.006 |
| 59 | 0.0125 |
| 63 | 0.0125 |
| 68 | 0.006 |

| Comparative agents: | % a.i. | % mort. |
|---|---|---|
| Demeton-S-methyl | 0.1 | 10 |
| Dimethoate | 0.1 | 20 |
| Azinphosmethyl |  | 0.1 |

[1)] = Tetranychus urticae-strain "Baardse" = (B)
[2)] = Concentration for 99–100% desruction of total pests
Demeton-S-methyl = O,O-dimethyl-S-(3-thiapentyl)-monothiophosphate
Dimethoate = O,O-dimethyl-S-(N-methyl-carbamoyl-methyl)dithiophosphate
Azinphosmethyl = O,O-dimethyl-S-(4-oxo-1,2,3-benzotriazin-3-methyl)-dithiophosphate

EXAMPLE III 50 larvae (4th stage) of the Mexican bean beetle (*Epilachna varivestis*) and leaves of the dwarf bean (*Phaseolus vulgaris*) were sprayed in a spraying apparatus with a measured quantity (corresponding to an application quantity of 600 l of spray liquor/ha in the open air) of the aqueous dilution of an emulsion concentrate that contained the active substance of Example 15 in a concentration of 0.002% by weight. The leaves with the beetle larvae were arranged in open containers at 22° C. In a check carried out 48 hours after spraying, 100% destruction of the test animals was observed.

The examples given in Table III proved equally effective in this test.

Table III

| Preparation according to Example | % by weight AS in the spray liquor | % mortality after 48 hours |
|---|---|---|
| 1 | 0.001 | 100 |
| 2 | 0.001 | 100 |
| 5 | 0.005 | 100 |
| 7 | 0.002 | 100 |
| 17 | 0.002 | 100 |
| 23 | 0.005 | 100 |
| 39 | 0.005 | 90 |
| 45 | 0.005 | 100 |
| 46 | 0.002 | 90 |
| 58 | 0.002 | 100 |
| 59 | 0.001 | 80 |
| 61 | 0.005 | 90 |
| 62 | 0.001 | 80 |

EXAMPLE IV

The action against aphids was proved by the following test arrangement: Horse beans (*Vicia faba*) infected with black bean aphids (*Doralis fabae*) were sprayed to drip-off with aqueous suspension of spray powder concentrates that contained the quantity of active substance given in Table IV. The plants were arranged in a greenhouse at 22° C.

Table IV

| Preparation according to Example | % by weight AS in the spray liquor | % destruction after 3 days |
|---|---|---|
| 1 | 0.0015 | 100 |
|  | 0.00075 | 95 |
| 2 | 0.0015 | 100 |
|  | 0.00075 | 85 |
| 3 | 0.0015 | 100 |
|  | 0.00075 | 95 |
| 4 | 0.003 | 100 |
|  | 0.0015 | 85 |
| 6 | 0.0015 | 100 |
|  | 0.00075 | 95 |
| 7 | 0.003 | 100 |
|  | 0.0015 | 95 |
| 8 | 0.0015 | 95 |
|  | 0.00075 | 85 |
| 9 | 0.0015 | 95 |
|  | 0.00075 | 85 |
| 10 | 0.0015 | 100 |
|  | 0.00075 | 98 |
| 11 | 0.00075 | 95 |
|  | 0.000375 | 90 |
| 12 | 0.006 | 95 |
|  | 0.003 | 80 |
| 14 | 0.003 | 100 |
|  | 0.0015 | 95 |
| 15 | 0.0015 | 100 |
|  | 0.00075 | 90 |
| 18 | 0.0015 | 100 |
|  | 0.00075 | 80 |
| 19 | 0.003 | 100 |
|  | 0.0015 | 80 |
| 20 | 0.003 | 100 |
|  | 0.0015 | 90 |
| 22 | 0.003 | 100 |
|  | 0.0015 | 70 |
| 24 | 0.003 | 100 |
|  | 0.0015 | 50 |
| 27 | 0.0015 | 100 |
|  | 0.00075 | 95 |

Table IV-continued

| Preparation according to Example | % by weight AS in the spray liquor | % destruction after 3 days |
|---|---|---|
| 28 | 0.003 | 100 |
|  | 0.0015 | 70 |
| 32 | 0.0015 | 100 |
|  | 0.00075 | 80 |
| 35 | 0.006 | 100 |
|  | 0.003 | 95 |
| 36 | 0.0125 | 100 |
|  | 0.006 | 80 |
| 38 | 0.003 | 95 |
|  | 0.0015 | 50 |
| 42 | 0.0125 | 100 |
|  | 0.006 | 90 |
| 43 | 0.0125 | 100 |
|  | 0.006 | 85 |
| 45 | 0.006 | 90 |
|  | 0.003 | 50 |
| 47 | 0.0125 | 100 |
|  | 0.006 | 85 |
| 48 | 0.006 | 100 |
|  | 0.003 | 80 |
| 50 | 0.006 | 100 |
|  | 0.003 | 80 |
| 51 | 0.0015 | 100 |
|  | 0.00075 | 80 |
| 53 | 0.006 | 100 |
|  | 0.003 | 50 |
| 55 | 0.006 | 100 |
|  | 0.003 | 90 |
| 58 | 0.0015 | 100 |
|  | 0.00075 | 80 |
| 59 | 0.006 | 100 |
|  | 0.003 | 90 |
| 60 | 0.003 | 100 |
|  | 0.0015 | 95 |
| 62 | 0.006 | 100 |
|  | 0.003 | 90 |
| 63 | 0.0015 | 90 |
|  | 0.00075 | 85 |
| 65 | 0.006 | 100 |
|  | 0.003 | 95 |
| 66 | 0.0125 | 100 |
|  | 0.006 | 90 |
| 67 | 0.0015 | 100 |
|  | 0.00075 | 90 |
| 68 | 0.003 | 100 |
|  | 0.0015 | 90 | humidity the number of galls were ascertained according to the following scheme:

Evaluation scheme:

| galls per plant | numerical value |
|---|---|
| 0 | 1 |
| 1–2 | 2 |
| 3–5 | 3 |
| 6–10 | 4 |
| 11–20 | 5 |
| 21–40 | 6 |
| 41–80 | 7 |
| 81–150 | 8 |
| above 150 | 9 |

Table V indicates the activity of the following preparations:

Table V

| Preparation according to Example | quantity of active substance per unit area kg/ha | numerical value |
|---|---|---|
| 7 | 20 | 2 |
| 39 | 10 | 1 |
| 40 | 20 | 1 |
| 41 | 20 | 3 |
| untreated sample |  | 9 |

EXAMPLE VI:

It is clear from German Auslegeschrift No. 1,122,935 that the compounds (Examples 7 and 8) mentioned in Table I of the DAS in comparison with the corresponding phosphonic acid ester according to the invention, have a clearly poorer miticidal potency in a spray test.

Table VI

| Preparation according to Example | Structural formula | Conc. % | Contact action against Tu in % |
|---|---|---|---|
| 7 (DAS 1.122.935) | $CH_3O$-$\overset{S}{\underset{\|}{P}}$-$S$-$CH_2$-$\overset{O}{\underset{\|}{C}}$-$\overset{CH_3}{\underset{\|}{N}}$-$C_6H_4$-$Cl$ ; $CH_3O$ | 0.02 0.01 | 100 100 |
| 8 (DAS 1.122.935) | $C_2H_5O$-$\overset{S}{\underset{\|}{P}}$-$S$-$CH_2$-$\overset{O}{\underset{\|}{C}}$-$\overset{CH_3}{\underset{\|}{N}}$-$C_6H_4$-$Cl$ ; $C_2H_5O$ | 0.02 0.01 | 100 100 |
| 9 (according to the invention) | $CH_3$-$\overset{S}{\underset{\|}{P}}$-$S$-$CH_2$-$\overset{O}{\underset{\|}{C}}$-$\overset{CH_3}{\underset{\|}{N}}$-$C_6H_4$-$Cl$ ; $C_2H_5O$ | 0.0015 0.00075 | 100 100 |

Tu = Tetranychus urticae

EXAMPLE V

A dust-type formulation was mixed with earth that was contaminated with nematodes of the type *Meloidogyne incognita*. This soil was then charged into pots and tomatoes planted therein. After 4 at 25° C. and 70% air

EXAMPLE VII

Cotton strainers (*Oncopeltus fasciatus*) are sprayed until drip-off with aqueous dilutions of spray powder concentrates that contain the quantity of active substance given in Table VII of the respective claimed compound. Subsequently in insects are arranged in containers provided with airpermeable lids at room temperature. The results are compiled in Table VII.

Table VII

| Preparation according to Example | % by weight AS in the spray liquor | % destruction after 5 days |
|---|---|---|
| 7 | 0.025 | 100 |
|  | 0.0125 | 70 |
| 9 | 0.025 | 100 |
|  | 0.0125 | 50 |
| 38 | 0.025 | 100 |
|  | 0.0125 | 60 |
| 39 | 0.0125 | 100 |
|  | 0.006 | 50 |
| 40 | 0.025 | 100 |
|  | 0.0125 | 85 |

We claim:

1. Insecticidal, miticidal and nematocidal agents consisting essentially of a compound of the formula I

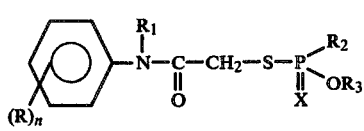

in which
R = identical or different substituents selected from the group halogen, $(C_1-C_6)$-alkyl, $(C_1-C_3)$-halogenoalkyl, NO, $(C_1-C_4)$-thioalkyl or $OCH_3$,
$R_1$ = isopropyl,
$R_2$ and $R_3$ = $(C_1-C_6)$-alkyl (identical or different),
X = oxygen or sulfur and
n = 1 or 2, and an inert carrier.

2. Compounds of the formula

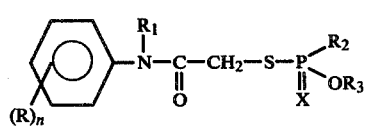

in which
R = identical or different substituents selected from the group halogen, $(C_1-C_6)$-alkyl, $(C_1-C_3)$-halogenoalkyl, $NO_2$, $(C_1-C_4)$-thioalkyl or $OCH_3$,
$R_1$ = isopropyl,
$R_2$ and $R_3$ = $(C_1-C_6)$-alkyl (identical or different),
X = oxygen or sulfur and
n = 1 or 2, 3. Compounds of the formula I in which R = F, Cl, Br, $(C_1-C_4)$-alkyl, $CF_3$, $NO_2$ or $S-CH_3$, $R_1$ = isopropyl, and
$R_2$ and $R_3$ = $(C_1-C_4)$-alkyl, and X and n have the meanings given in claim 2.

4. Compound of the formula

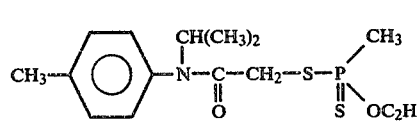

5. Compound of the formula

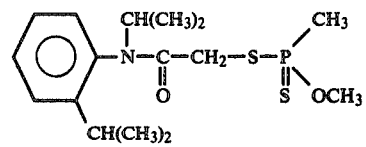

6. Compound of the formula

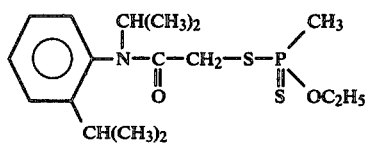

7. Compound of the formula

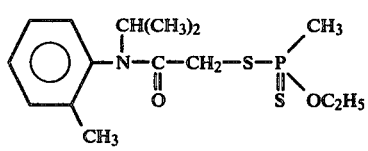

8. Compound of the formula

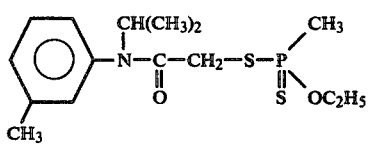

9. Compound of the formula

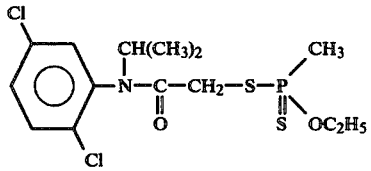

10. Compound of the formula

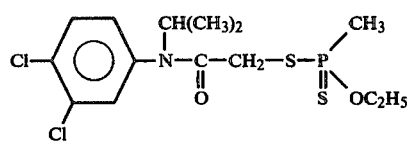

11. Compound of the formula

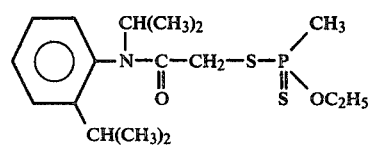

* * * * *